United States Patent
Tsuneoka et al.

(10) Patent No.: US 11,420,913 B2
(45) Date of Patent: Aug. 23, 2022

(54) METHOD FOR PRODUCING MONOCYCLIC AROMATIC HYDROCARBON HAVING 6-8 CARBON ATOMS

(71) Applicants: ENEOS CORPORATION, Tokyo (JP); THE UNIVERSITY OF TOKYO, Tokyo (JP); KOGAKUIN UNIVERSITY, Tokyo (JP)

(72) Inventors: Hideo Tsuneoka, Tokyo (JP); Yasuyuki Iwasa, Tokyo (JP); Yasuhiro Araki, Tokyo (JP); Kazu Okumura, Tokyo (JP); Masaru Ogura, Tokyo (JP)

(73) Assignees: ENEOS CORPORATION, Tokyo (JP); THE UNIVERSITY OF TOKYO, Tokyo (JP); KOGAKUIN UNIVERSITY, Tokyo (JP)

( * ) Notice: Subject to any disclaimer, the term of this patent is extended or adjusted under 35 U.S.C. 154(b) by 0 days.

(21) Appl. No.: 17/272,787

(22) PCT Filed: Sep. 2, 2019

(86) PCT No.: PCT/JP2019/034367
§ 371 (c)(1),
(2) Date: Mar. 2, 2021

(87) PCT Pub. No.: WO2020/050199
PCT Pub. Date: Mar. 12, 2020

(65) Prior Publication Data
US 2021/0214288 A1    Jul. 15, 2021

(30) Foreign Application Priority Data
Sep. 3, 2018   (JP) .............................. JP2018-164608

(51) Int. Cl.
*C07C 2/12*         (2006.01)
*C10G 35/095*    (2006.01)
*C07C 15/04*       (2006.01)
*C07C 15/06*       (2006.01)
*C07C 15/08*       (2006.01)

(52) U.S. Cl.
CPC .............. *C07C 2/12* (2013.01); *C10G 35/095* (2013.01); *C07C 15/04* (2013.01); *C07C 15/06* (2013.01); *C07C 15/08* (2013.01); *C07C 2529/70* (2013.01)

(58) Field of Classification Search
None
See application file for complete search history.

(56) References Cited

U.S. PATENT DOCUMENTS

| 4,933,310 | A  | * | 6/1990 | Aufdembrink | ........ | B01J 29/049 |
|||||||502/64|
| 5,800,696 | A  |   | 9/1998 | Drake et al. |||
| 11,066,309 | B2 | * | 7/2021 | Tsapatsis | ................ | C01B 39/04 |
| 2002/0072642 | A1 | * | 6/2002 | Allison | .................... | B01J 37/18 |
|||||||585/418|
| 2002/0082460 | A1 | * | 6/2002 | Verduijn | ................. | C07C 2/864 |
|||||||585/475|
| 2010/0185034 | A1 | * | 7/2010 | Nishimura | ........... | B01J 29/7876 |
|||||||585/420|
| 2012/0142986 | A1 | * | 6/2012 | Okabe | ....................... | C07C 2/76 |
|||||||585/418|

FOREIGN PATENT DOCUMENTS

| EP | 3 841 092 A2 | 5/1998 |
| JP | H10-147543 A | 6/1998 |
| JP | H10-151351 A | 6/1998 |
| JP | 2008-037803 A | 2/2008 |
| JP | 2008-038032 A | 2/2008 |
| JP | 2009-233601 A | 10/2009 |
| WO | 2018/038169 A1 | 3/2018 |

OTHER PUBLICATIONS

Nov. 19, 2019 Search Report issued in International Patent Application No. PCT/JP2019/034367.

* cited by examiner

*Primary Examiner* — Tam M Nguyen
(74) *Attorney, Agent, or Firm* — Oliff PLC

(57) ABSTRACT

A method for producing a monocyclic aromatic hydrocarbon having 6 to 8 carbon atoms, including bringing a raw material which contains a light hydrocarbon having 2 to 7 carbon atoms as a main component into contact with a catalyst composition for producing a monocyclic aromatic hydrocarbon having 6 to 8 carbon atoms. The catalyst composition for producing a monocyclic aromatic hydrocarbon having 6 to 8 carbon atoms is coated with an amorphous silicon oxide compound and contains a crystalline aluminosilicate, and the silicon oxide compound is a silicon oxide compound derived from a compound represented by $X_n Si(OR)_{4-n}$, where X represents a hydrogen atom or an alkyl group, R represents an alkyl group, and n represents an integer of 0 to 4.

6 Claims, No Drawings

METHOD FOR PRODUCING MONOCYCLIC AROMATIC HYDROCARBON HAVING 6-8 CARBON ATOMS

TECHNICAL FIELD

The present invention relates to a method for producing a monocyclic aromatic hydrocarbon having 6 to 8 carbon atoms.

Priority is claimed on Japanese Patent Application No. 2018-164608, filed on Sep. 3, 2018, the content of which is incorporated herein by reference.

BACKGROUND ART

Conventionally, catalytic reforming of straight naphtha using a platinum/alumina-based catalyst has been widely adopted as a method for obtaining gasoline or an aromatic hydrocarbon, which has a high octane value. As the raw material naphtha in this catalytic reforming, a fraction having a boiling point of 70° C. to 180° C. is mainly used for the purpose of producing gasoline for automobiles. In addition, in the case of producing aromatic fractions such as benzene, toluene, and xylene, so-called BTX, a fraction of 60° C. to 150° C. is used.

However, as the number of carbon atoms of the raw material hydrocarbon decreases, the conversion rate to aromatics decreases, and the octane value of the product also decreases. Therefore, in the conventional catalytic reforming method in which a light hydrocarbon containing a hydrocarbon having 7 or fewer carbon atoms as a main component has been used as a raw material, it has been difficult to produce gasoline having a high octane value and an aromatic hydrocarbon in high yield. As a result, the use of such light hydrocarbons has been limited to petrochemical raw materials and raw materials for producing city gas.

For this reason, attempts have been made to produce an aromatic hydrocarbon from the light hydrocarbon. For example, Patent Documents 1 to 3 disclose a method for producing an aromatic hydrocarbon by using a hydrocarbon having 2 to 7 carbon atoms as the main raw material and a gallium-containing crystalline aluminosilicate catalyst composition.

It is preferable that a monocyclic aromatic hydrocarbon having 6 to 8 carbon atoms, which has a high added value, can be produced in high yield. In order to obtain a monocyclic aromatic hydrocarbon having 6 to 8 carbon atoms, which has a high added value, in a further higher yield, there is still room for improvement in the catalyst compositions for producing a monocyclic aromatic hydrocarbon, such as those disclosed in Patent Documents 1 to 3.

CITATION LIST

Patent Document

[Patent Document 1]
Japanese Unexamined Patent Application, First Publication No. 2008-37803
[Patent Document 2]
Japanese Unexamined Patent Application, First Publication No. 2008-38032
[Patent Document 3]
Japanese Unexamined Patent Application, First Publication No. 2009-233601

SUMMARY OF INVENTION

Technical Problem

The present invention has been made in consideration of the above circumstances, and an object of the present invention is to provide a method for producing a monocyclic aromatic hydrocarbon having 6 to 8 carbon atoms in high yield by using, as a raw material, a light hydrocarbon containing a hydrocarbon having 7 or fewer carbon atoms as a main component.

Solution to Problem

The crystalline aluminosilicate has an acidic point as the active site in Al, and this acidic point contributes to the catalytic reforming reaction. However, coke is gradually formed and accumulated as the reaction proceeds, whereby the activity thereof deteriorates.

As a result of performing diligent studies to solve the above problems, the inventors of the present invention have found that in a case where acidic points of a crystalline aluminosilicate are coated with a specific silicon oxide compound, a monocyclic aromatic hydrocarbon having 6 to 8 carbon atoms can be produced in high yield by using, as a raw material, a light hydrocarbon containing a hydrocarbon having 7 or fewer carbon atoms as a main component, and have completed the present invention.

A first aspect of the present invention is a method for producing a monocyclic aromatic hydrocarbon having 6 to 8 carbon atoms, the method including bringing a raw material which contains a light hydrocarbon having 2 to 7 carbon atoms as a main component into contact with a catalyst composition for producing a monocyclic aromatic hydrocarbon having 6 to 8 carbon atoms, in which the catalyst composition for producing a monocyclic aromatic hydrocarbon having 6 to 8 carbon atoms is coated with an amorphous silicon oxide compound and contains a crystalline aluminosilicate, and the silicon oxide compound is a silicon oxide compound derived from a compound represented by Formula (1).

$$X_n Si(OR)_{4-n} \quad (1)$$

[In the formula, X represents a hydrogen atom or an alkyl group, R represents an alkyl group, and n represents an integer of 0 to 4.]

Another aspect of the present invention is a method for producing a monocyclic aromatic hydrocarbon having 6 to 8 carbon atoms, the method including a step of heating a catalyst composition containing a crystalline aluminosilicate and a compound represented by General Formula (1) at room temperature to 110° C. in the absence of oxygen to obtain a reaction product and a step of heating the reaction product at 300° C. to 600° C. in the presence of oxygen.

$$X_n Si(OR)_{4-n} \quad (1)$$

[In the formula, X represents a hydrogen atom or an alkyl group, R represents an alkyl group, and n represents an integer of 0 to 4.]

Advantageous Effects of Invention

According to the present invention, a method for producing a monocyclic aromatic hydrocarbon having 6 to 8 carbon atoms in high yield by using, as a raw material, a light hydrocarbon containing a hydrocarbon having 7 or fewer carbon atoms as a main component is provided.

DESCRIPTION OF EMBODIMENTS

<Catalyst Composition for Producing Monocyclic Aromatic Hydrocarbon Having 6 To 8 Carbon Atoms>

In the present embodiment, a catalyst composition for producing a monocyclic aromatic hydrocarbon having 6 to 8 carbon atoms (hereinafter, may be referred to as a "catalyst composition (A)") contains a crystalline aluminosilicate and is coated with a silicon oxide compound.

(Silicon Oxide Compound)

In the present embodiment, the silicon oxide compound is a general term for compounds containing a siloxane bond (a Si—O—Si bond). However, in the present embodiment, the crystalline aluminosilicate is not included in the silicon oxide compound.

The silicon oxide compound for the catalyst composition (A) is amorphous. In a case where the catalyst composition (A) is coated with the amorphous silicon oxide compound, the thickness of the coating layer can be adjusted to be thin as compared with the case of a crystalline silicon oxide compound, and the reaction activity of the catalyst before coating is easily maintained, which is preferable.

In the present embodiment, the silicon oxide compound is a silicon oxide compound derived from a compound represented by Formula (1).

$$X_n Si(OR)_{4-n} \quad (1)$$

[In the formula, X represents a hydrogen atom or an alkyl group, R represents an alkyl group, and n represents an integer of 0 to 4.]

In General Formula (1), X represents a hydrogen atom or an alkyl group. Examples of the alkyl group as X include a linear or branched alkyl group having 1 to 10 carbon atoms. For example, tetramethoxysilane, tetraethoxysilane, $SiOCH_3(CH_3)_3$, $Si(OCH_3)_2(CH_3)_2$, $Si(OCH_3)_3(CH_3)$, and $SiOCH_3(C_3H_7)_3$ are mentioned. Among them, the compound represented by General Formula (1) is preferably tetramethoxysilane or tetraethoxysilane.

The method for coating the catalyst composition with the silicon oxide compound is not particularly limited, and examples thereof include a method for surface-treating the catalyst composition with the compound represented by General Formula (1).

Specifically, the catalyst composition containing a crystalline aluminosilicate and the compound represented by General Formula (1) are heated and stirred in a nitrogen atmosphere at room temperature to 110° C. (preferably 50° C. to 100° C.), and further stirred for 1 to 5 hours (preferably 1 to 2 hours). Then, the reaction product is then filtered, washed with an organic solvent such as hexane, cyclohexane, or dodecane, and dried. Next, the catalyst composition (A) coated with the silicon oxide compound is obtained by heat treatment at 300° C. to 600° C. (preferably 450° C. to 600° C.) in the presence of oxygen.

In the catalyst composition (A) of the present embodiment, the molar ratio of Al to the acid quantity of the catalyst, which is defined by the amount of ammonia desorbed in a temperature range of 200° C. to 500° C. in the $NH_3$-TPD method, is preferably 1.25 or less, more preferably 1.23 or less, and still more preferably 1.21 or less. Further, in terms of practical use, the molar ratio is preferably 0.50 or more. The acid quantity in the catalyst composition (A) is derived from the total amount of Al in the outer surface and the pores of the catalyst composition. In a case where Al on the outer surface is coated by surface treatment, and the rate between the acid quantity of the catalyst and the molar ratio of Al is controlled to a predetermined rate, it is possible to improve the yield of aromatics while suppressing side reactions such as the formation of heavier products and maintaining the cyclization reaction activity.

Further, the acid quantity of the catalyst, which is defined by the amount of ammonia desorbed in a temperature range of 200° C. to 500° C. in the $NH_3$-TPD method, is preferably 1.00 μmol/g or less and more preferably 0.50 μmol/g or less. In a case where the acidic points on the surface of the catalyst are adjusted to an appropriate density, it is possible to suppress the reaction of forming heavier products from the raw material and improve the yield of the monocyclic aromatic hydrocarbon having 6 to 8 carbon atoms.

In a case where the acid quantity of the catalyst, which is defined by the amount of ammonia desorbed in a temperature range of 200° C. to 500° C. in the $NH_3$-TPD method, is equal to or less than the above upper limit value, side reactions such as the formation of heavier products and gas decomposition are suppressed, and thus the yield of aromatics is improved. Further, the acid quantity of the catalyst, which is defined by the amount of ammonia desorbed in a temperature range of 200° C. to 500° C. in the $NH_3$-TPD method is equal to or more than the above lower limit value, the effect of the reduction of the reaction active site due to coating is not affected, and thus aromatics can be obtained in high yield.

In the present specification, the acid quantity of the catalyst indicates the quantity of the acidic point of the catalyst measured by the $NH_3$-TPD method.

The $NH_3$-TPD method is a method in which ammonia ($NH_3$), which is a base probe molecule, is adsorbed on a catalyst, and then the amount of ammonia that is desorbed by continuously increasing the temperature and the desorption temperature are measured to measure the quantity of the acidic point of the catalyst.

The $NH_3$-TPD method can be carried out, for example, using the device under the measurement conditions described in "NIWA; Zeolite, 10, 175 (1993)".

(Crystalline Aluminosilicate)

In the present embodiment, the structure of the crystalline aluminosilicate contained in the catalyst composition (A) is not particularly limited; however, a pentasil type zeolite is preferable. Among them, a zeolite having an MFI type and/or MEL type crystal structure is more preferable (the crystalline aluminosilicate having a three-dimensionally linked structure is referred to as the zeolite). The MFI type and MEL type zeolites belong to the conventionally known zeolite structure types published by "The Structure Commission of the International Zeolite Association" (Atlas of Zeolite Structure Types, W. M. Meiyer and D. H. Olson (1978). Distributed by Polycrystal Book Service, Pittsburgh, Pa., USA).

An example of the MFI type zeolite is ZSM-5, and an example of the MEL type zeolite is ZSM-11.

In the present embodiment, as the crystalline aluminosilicate contained in the catalyst composition (A), a crystalline aluminosilicate in which gallium or zinc is present, a crystalline aluminosilicate on which gallium or zinc is supported (hereinafter referred to as a "gallium-supporting crystalline aluminosilicate" or a "zinc-supporting crystalline aluminosilicate"), or a crystalline aluminosilicate in which gallium or zinc is present and on which gallium or zinc is supported can be used. However, a crystalline aluminosilicate containing gallium or zinc at least therein is preferable. Further, a crystalline aluminosilicate containing a gallium cation or a zinc cation therein is more preferable.

In the present embodiment, the crystalline aluminosilicate contained in the catalyst composition (A) is preferably produced by inserting gallium or zinc into a crystalline aluminosilicate by an ion exchange method. Examples of the ion exchange method include a method in which a gallium source or zinc source is used in the form of a solution (in many cases, an aqueous solution) and a crystalline aluminosilicate is immersed in the solution or a method in which a crystalline aluminosilicate and a gallium source or a zinc source are physically mixed in a solid state to perform ion exchange.

In this case, as the gallium source, a gallium salt such as gallium nitrate or gallium chloride, gallium oxide, or the like can be preferably used. In the case of a water-reactive material such as gallium chloride or solid gallium oxide, a method in which a crystalline aluminosilicate and a gallium source are physically mixed in a solid state to perform ion exchange is preferable. Similarly, as the zinc source, zinc nitrate, zinc chloride, or zinc oxide can be preferably used. Further, in a case of performing ion exchange, a method of heating in an atmosphere of a reducing gas, an inert gas, or a mixed gas containing them is preferable.

In the present embodiment, the particle size of the crystalline aluminosilicate contained in the catalyst composition (A) is preferably 0.05 to 20 μm, more preferably 0.1 to 10 μm, still more preferably 0.5 to 5 μm, and even still more preferably 1 to 3 μm. Further, the content of particles having the above particle size is preferably 80% by mass or more based on the mass of all particles.

In a case where the size of the reaction molecule and the pore size of the crystalline aluminosilicate are substantially the same, the diffusion rate of the molecule tends to be low in the crystalline aluminosilicate pores. Accordingly, in a case where the particle size is 20 μm or less, the reaction molecule easily approaches the active site in the deep portion of the pore, and thus the active site is easily used effectively during the reaction.

In a case where the crystalline aluminosilicate is obtained by hydrothermal synthesis, examples of the factor that affects the size of the produced particle include the kind of silica source, the amount of an organic additive such as a quaternary ammonium salt, the amount or kind of an inorganic salt as a mineralizing agent, the base quantity in a gel, the pH of a gel and the temperature raising rate during the crystallization operation, the temperature, and the stirring rate. In a case where these conditions are appropriately adjusted, a crystalline aluminosilicate having a particle size in the above range can be obtained.

In the present embodiment, the silica/alumina ratio (the molar ratio of silicon to aluminum) of the crystalline alumina silicate is preferably 10 or more and 1,000 or less and more preferably 35 or more and 100 or less.

In the present embodiment, the content of gallium with respect to 100 parts by mass of the catalyst composition (A) is preferably 0.1 part by mass or more and 10.0 parts by mass or less, more preferably 1.0 part by mass or more and 7.0 parts by mass or less, and still more preferably 2.0 parts by mass or more and 5.0 parts by mass or less.

The molar ratio of gallium to aluminum (atomic ratio, Ga/Al) is preferably 0.1 or more and 10.0 or less, more preferably 0.5 or more and 7.0 or less, and particularly preferably 1.0 or more and 5.0 or less.

Activation treatment

Further, in the present embodiment, the crystalline aluminosilicate contained in the catalyst composition (A) can be subjected, as desired, to various activation treatments, which are generally performed in a case where a crystalline aluminosilicate is used as a catalyst component. That is, the crystalline aluminosilicate contained in the catalyst composition (A) includes not only those produced by the method such as the hydrothermal synthesis but also those obtained by the modification treatment or activation treatment thereof.

For example, after performing ion exchange of the crystalline aluminosilicate in an aqueous solution containing an ammonium salt such as ammonium chloride, ammonium fluoride, ammonium nitrate, or ammonium hydroxide to form an ammonium type crystalline aluminosilicate, it is possible to introduce a desired metal other than the alkali metal or the alkaline earth metal by performing ion exchange in an aqueous solution containing a metal ion other than the alkali metal ion or the alkaline earth metal ion or impregnating the aqueous solution.

Further, in a case of being heated in air, or in a nitrogen or hydrogen atmosphere at a temperature of 200° C. to 800° C. and preferably at a temperature of 350° C. to 700° C., for 3 to 24 hours to remove ammonia, the ammonium type crystalline aluminosilicate can be activated to have an acid type structure. In addition, the acid type catalyst may be treated with hydrogen or a mixed gas of hydrogen and nitrogen under the above conditions. Further, the acid type catalyst may be subjected to ammonia modification in which the acid type catalyst is brought into contact with ammonia under dry conditions. Generally, it is preferable that the catalyst composition (A) is used after being subjected to the above-described activation treatment before being brought into contact with the hydrocarbon raw material.

In the present embodiment, the active component of the catalyst composition (A) is the crystalline aluminosilicate; however, the catalyst composition may contain a carrier, a molding aid, or the like for the purpose of facilitating molding or improving the mechanical strength of the catalyst.

In a case where a carrier, a molding aid, or the like is contained, the content of the crystalline aluminosilicate occupied in the total mass of the catalyst composition is not particularly limited; however, the crystalline aluminosilicate is preferably 40% to 95% by mass, more preferably 50% to 90% by mass, and still more preferably 60% to 80% by mass, with respect to the total mass of the catalyst composition (A).

The composition the containing crystalline aluminosilicate is formed into various molded bodies having a shape such as a granule shape, a sphere shape, a plate shape, or a pellet shape by extrusion molding, spray drying, tableting molding, rolling granulation, in-oil granulation, or the like. Further, at the time of molding, it is desirable to use an organic compound type lubricant in order to improve the moldability.

In general, a composition of a crystalline aluminosilicate can be molded before being subjected to the ion exchange step for the crystalline aluminosilicate by using ammonium ions or the like, or the crystalline aluminosilicate can be molded after being subjected to the ion exchange.

Additive

Further, in the present embodiment, the catalyst composition (A) may contain an additive in addition to the above-described crystalline aluminosilicate. The additive is not particularly limited, and examples thereof include an inorganic oxide such as alumina boria, silica, silica alumina, or aluminum phosphate, a clay mineral such as kaolin or montmorillonite, and an inorganic phosphorus compound, and an organic phosphorus compound. The amount of the additive to be added is not particularly limited; however, the additive is added in the catalyst composition so that the content thereof is 50% by mass or less, more preferably 30% by mass or less, and still more preferably 15% by mass or less.

Further, in the present embodiment, a metal component as an auxiliary component can be supported in the catalyst composition (A) and used. The metal component as an auxiliary component may be supported on a crystalline aluminosilicate, may be supported on other additives, or may be supported on a crystalline aluminosilicate and other additives.

Examples of such an auxiliary metal component include a metal having a dehydrogenating ability and a metal having an effect of suppressing carbon precipitation. Specific examples of the auxiliary metal components include magnesium, calcium, strontium, barium, lantern, cerium, praseodymium, neodymium, samarium, europium, gadolinium, terbium, dysprosium, holmium, erbium, thulium, ytterbium, lutetium, titanium, vanadium, chromium, molybdenum, tungsten, manganese, rhenium, iron, ruthenium, cobalt, rhodium, iridium, nickel, palladium, platinum, copper, silver, zinc, aluminum, indium, germanium, tin, lead, phosphorus, antimony, bismuth, and selenium. These metals can be used alone or in a combination of two or more thereof, and the amount of the supported metal is 0.1% to 10% by mass in terms of metal. As the metal supporting method, conventionally known techniques such as an ion exchange method, an impregnation method, and physical mixing can be used. Further, when the pentasil type zeolite is synthesized, an auxiliary component metal can be incorporated by adding the above-described metal component as an auxiliary component. In addition, as the auxiliary metal component that has the effect of suppressing the accumulation of coke during the reaction, one or more kinds of metals selected from magnesium, calcium, lantern, cerium, praseodymium, neodymium, samarium, europium, gadolinium, terbium, dysprosium, holmium, erbium, thulium, ytterbium, lutetium, ruthenium, and ytterbium can be supported, and the amount of the supported metal is 0.01% to 5% by mass in terms of metal.

<Method for Producing Monocyclic Aromatic Hydrocarbon Having 6 To 8 Carbon Atoms>

In the method for producing an aromatic hydrocarbon of the present embodiment, the above-described catalyst composition (A) is brought into contact with a raw material oil containing a hydrocarbon having 2 to 7 carbon atoms to produce an aromatic hydrocarbon.

Here, the raw material used in the present embodiment contains a light hydrocarbon having 2 to 7 carbon atoms, and the content of the light hydrocarbon having 2 to 7 carbon atoms in the raw material is not particularly limited; however, it is preferably 20% by mass or more, more preferably 40% by mass or more, and particularly preferably 60% to 100% by mass.

The light hydrocarbon having 2 to 7 carbon atoms is not particularly limited; however, it may be linear, branched, or cyclic, and it may be paraffin or olefin. In addition, a mixture of thereof may be used. Specific examples of such hydrocarbons include linear saturated aliphatic hydrocarbons having 2 to 7 carbon atoms (ethane, propane, normal butane, normal pentane, normal hexane, and normal heptane), branched saturated aliphatic hydrocarbons (isobutane, 2-methylbutane, 2,2-dimethylbutane, 2-methylpentane, 3-methylpentane, 2,3-dimethylbutane, 2-methylhexane, 3-methylhexane, 2, 2-dimethylpentane, 2,3-dimethylpentane, 2,4-dimethylpentane, and 2,2,3-trimethylbutane), cyclic saturated aliphatic hydrocarbons (cyclopropane, cyclobutane, cyclopentane, 1-methylcyclopentane, 1,1-dimethylcyclopentane, 1,2-dimethylcyclopentane, 1,3-dimethylcyclopentane, cyclohexane, and methylcyclohexane), linear unsaturated aliphatic hydrocarbons (ethylene, propylene, normal butene, normal pentene, normal hexene, and normal heptene), branched unsaturated aliphatic hydrocarbons (isobutene, 2-methylbutene, 2-methylpentene, 3-methylpentene, 2-methylhexene, and 3-methylhexene), cyclic unsaturated aliphatic hydrocarbons (cyclopentene, methylcyclopentene, cyclohexene, and methylcyclohexene), a liquefied petroleum gas containing propane and butane as main components, a light fraction (light naphtha) in naphtha fraction, which has a boiling point of 100° C. or less and contains paraffin having 5 to 7 carbon atoms as a main component, a C4 fraction from a fluid catalytic cracking (FCC) device, and raffinate of a ethylene cracker.

Next, the steps of the method for producing a monocyclic aromatic hydrocarbon of the present embodiment are not particularly limited; however, it is preferable to mainly have the following four steps (a) to (d). Further, in addition to the following four steps (a) to (d) of the method for producing a monocyclic aromatic hydrocarbon of the present embodiment, a step (e) may be included.

(a) Conversion reaction step
(b) Step of performing gas-liquid separation of reaction layer effluent
(c) Step of separating hydrogen from separation gas
(d) Step of separating aromatic hydrocarbon from separation liquid
(e) Step of mixing raw material light hydrocarbon with recycled gas (Conversion Reaction Step)

For this step, at least n pieces of reaction layers retaining at least the catalyst composition (A) described above are arranged in series, and further, a heating furnace or the like is provided between the reaction layers as means for heating an effluent from the reaction layer. The conversion reaction step is a step of passing a mixture of a light hydrocarbon as a raw material with a recycled gas described later through a reaction layer and converting the mixture to an aromatic hydrocarbon. The preferred reaction conditions in this step are a reaction layer inlet temperature of 350° C. to 650° C., a hydrogen partial pressure of 0.5 MPa or less, and a gas space velocity of a raw material of 100 to 2,000 hr$^{-1}$.

The reaction layer inlet temperature in the conversion reaction step according to the present embodiment is generally preferably in the range of 350° C. to 650° C. However, in a case where the light hydrocarbon as a raw material contains normal paraffin as a main component, the temperature is more preferably 450° C. to 650° C., in a case of containing normal paraffin as a main component, the temperature is still more preferably 400° C. to 600° C., and in a case of containing olefin as a main component, the temperature is even still more preferably 350° C. to 550° C.

The reactor that is used in the conversion reaction step is not particularly limited, and examples thereof include a fixed bed type reactor, a CCR type reactor, and a fluidized bed type reactor. In a case where a fixed bed or a CCR type reactor is used, it is preferable that n pieces of reaction layers (n is an integer of 2 or more) retaining the catalyst composition (A) described above are arranged at least in series, and further, a heating device such as a heating furnace is provided between the reaction layers or in the reaction layer as means for heating an effluent from the reaction layer. In a case where the light hydrocarbon as a raw material contains olefin as a main component, the amount of heat absorbed is reduced, and thus the reaction layer retaining the catalyst composition (A) may be one layer (n=1).

Further, the first reaction layer among n pieces of reaction layers arranged in series is preferably arranged so that the catalyst amount in the first reaction layer is 30% by volume or less of the total catalyst amount, preferably 1% to 30% by volume, more preferably 2% to 30% by volume, and still more preferably 2% to 28% by volume. In a case where the number n of the reaction layers arranged in series is 3 or more, it is preferable that the catalyst amount in the first reaction layer is 60/n % by volume or less of the total amount of the catalyst. As a result, the final yield of aromatics is improved. The number n of the reaction layers is not particularly limited as long as it is 2 or more; however, in a case where the number is too large, the effect does not change, and the economic efficiency is bad. Accordingly, n is preferably 2 or more and 8 or less and more preferably 3 or more and 6 or less.

Further, in the conversion reaction step according to the present embodiment, the operation can be performed at the predetermined reaction layer inlet temperature, or the operation can be performed by continuously or stepwisely raising the reaction layer inlet temperature to obtain the predetermined yield of aromatics. In a case where the yield of aromatics falls below the predetermined range or the reaction layer inlet temperature exceeds the predetermined temperature range, the reactor is switched to a reactor filled with a new catalyst or a reactor filled with a regenerated catalyst, and then the reaction is continued. The regeneration of the catalyst can be carried out by heating treatment at 200° C. to 800° C. preferably 350 to 700° C., in the air stream such as air, nitrogen, hydrogen, or a nitrogen/hydrogen mixed gas. The method for producing an aromatic hydrocarbon of the present embodiment is preferably carried out using two or more series of fixed bed reaction devices including a reaction layer retaining the catalyst composition (A). In this case, each series of reaction devices is composed of a plurality of reaction layers that are arranged in series. The catalyst in one or more series of reactors is subjected to the regeneration treatment while a raw material containing a light hydrocarbon is introduced into the other one or more series of reactors to promote the reaction. With these two or more series of reactors, the reaction operation is carried out for 1 to 10 days using one or more series of reactors, and then the used reactors are switched to other one or more series of reactors that have been subjected to the regeneration treatment for 2 to 20 days, to perform reaction/regeneration, whereby continuous operation can be performed, for example, for one year.

Further, as in the cyclic operation, it is also possible to switch a part or all of the reactors of the series that are used for the reaction to other series to continue the reaction. Then, it is preferable to raise the reaction temperature continuously or stepwise by about 5° C. to 20° C. for each cycle of the reaction for 1 to 10 days to maintain the yield of aromatics in a predetermined range of 40% to 75% by weight.

The yield R of aromatics is represented by the following formula (1).

$$R = A/B \times 100 \, (\%) \quad (1)$$

A: Mass of aromatic hydrocarbon having 6 to 8 carbon atoms in conversion reaction product
B: Mass of all converted reaction products and unreacted hydrocarbon raw material In a case where an aliphatic and/or alicyclic hydrocarbon is converted to an aromatic hydrocarbon, a reaction involving dehydrogenation proceeds, and thus under the conditions of such a reaction, a hydrogen partial pressure commensurate with the reaction can be obtained without adding hydrogen. The intentional addition of hydrogen has the advantage of suppressing the accumulation of coke and reducing the frequency of regeneration; however, it is not always advantageous because the yield of aromatics decreases drastically as the hydrogen partial pressure increases. For this reason, the hydrogen partial pressure is preferably suppressed to 0.5 MPa or less.

In the conversion reaction step according to the present embodiment, it is desirable that a light gas containing methane and/or ethane, which is circulated as a recycled gas from the subsequent separation step, is allowed to be present. In a case where the conversion reaction is carried out in the presence of the light gas containing methane and/or ethane, the precipitation of coke on the catalyst can be suppressed, and thus the yield of aromatics can be maintained high for a long period of time. The amount of total light gas (recycled gas) circulated to the reaction system per 1 part by mass of the hydrocarbon supplying raw material is preferably 0.1 to 10 parts by mass and preferably 0.5 to 3 parts by mass.

(Step of Performing Gas-Liquid Separation of Reaction Layer Effluent)

In this step, the effluent from the conversion reaction step is introduced into a gas-liquid separation zone composed of one or more gas-liquid separators, and gas-liquid separation is performed under relatively high pressure to separate the effluent into a liquid component (high-pressure separation liquid) containing an aromatic hydrocarbon as a main component and a light gas (high-pressure separation gas) such as hydrogen, methane, ethane, propane, and butane. As the separation conditions, the temperature is generally 10° C. to 50° C. and preferably 20° C. to 40° C., and the pressure is generally 0.5 to 8 MPa and preferably 1 to 3 MPa.

The reaction layer effluent is cooled to 30° C. to 50° C. by indirect heat exchange with a low-temperature raw material hydrocarbon before being introduced into this gas-liquid separation step, and as necessary, a part of the light gas can be separated to reduce the load of the process of separating hydrogen from the gas-liquid separation step and the light gas.

For example, the cooled reaction layer effluent can be subjected to gas-liquid separation at a low pressure of 0.2 to 0.35 MPa using a low-pressure gas-liquid separator before being introduced into the gas-liquid separation step. Next, the column top gas of the low-pressure gas-liquid separator is compressed, cooled, and subjected to gas-liquid separation by repeating 2 to 3 times, the pressure of the column bottom liquid in the low-pressure gas-liquid separator is raised to 1 to 3 MPa, and the column top gas and the column bottom liquid are allowed to join with each other and subsequently can be introduced into the gas-liquid separation step. Further, it is also possible to perform introduction into the gas-liquid separation step after a condensate generated when the column top gas is compressed and the column bottom liquid are allowed to join with each other without allowing the column top gas and the column bottom liquid to join with each other.

(Step of Separating Hydrogen From Separation Gas)

In this step, hydrogen is selectively separated from the high-pressure separation gas separated in the gas-liquid separation step and a recycled gas containing methane and/or ethane is obtained. As the hydrogen separation method for this case, a conventionally known method such as a membrane separation method or a cryogenic separation method is used. The membrane separation method is preferable from the viewpoint of the efficiency of selective separation of hydrogen, but in a case where off-gas from the cryogenic separation method is used as a recycled gas, the unreacted propane can be reacted to the maximum as compared with the off-gas from the membrane separation method, which provides an advantage that the yield of the aromatic hydrocarbon can be increased by 1% to 3% by mass. Which method to use is determined from an economic point of view. As the membrane separation device, for example, a separation membrane using polyimide, polysulfone, or a blending product of polysulfone and polydimethylsiloxane is commercially available. A part of the recycled gas obtained in this step is discharged to the outside of the system in order to keep the total circulating gas amount within a certain range. In order to recover high-purity hydrogen, a membrane separation device or adsorption/desorption separation device (PSA) as a recovery system is preferably installed at the rear part of the membrane separation device. The choice of device in the rear part is decided from an economic point of view.

(Step of Separating Aromatic Hydrocarbon From Separation Liquid)

In this step, an aromatic hydrocarbon and a low boiling point hydrocarbon gas are separated from the high-pressure separation liquid obtained in the gas-liquid separation step, and a stabilizer (distillation column) is used as the separation device. The low boiling point hydrocarbon gas separated as the column top fraction is composed of C3 to C4 hydrocarbons and may be used as a recycled gas. Since the column bottom fraction contains a BTX fraction and a heavy fraction having 9 or more carbon atoms, BTX is further purified and recovered.

(Step of Mixing Raw Material Light Hydrocarbon With Recycled Gas)

This step is an optional step in which a raw material light hydrocarbon is mixed with the recycled gas containing methane and/or ethane, which is obtained in the hydrogen gas separation step and the low boiling point hydrocarbon gas separated in the aromatic hydrocarbon separation step, and the mixing can be performed in the pipe. This mixture is introduced into the conversion reaction step. The mixing rate of the recycled gas and the low boiling point hydrocarbon gas per 1 part by mass of the raw material light hydrocarbon is 0.1 to 10 parts by mass and preferably 0.5 to 3 parts by mass. In a case where methane and/or ethane is used as a recycled gas in this manner, the following effects can be obtained. That is, the aromatization reaction by cyclodehydrogenation is an endothermic reaction, which lowers the catalyst layer temperature and is disadvantageous to the aromatization reaction. Methane and/or ethane does not become aromatic under this reaction conditions and thus is regarded as an inert gas. In a case of being heated, methane and/or ethane acts as a heat supplying medium, suppresses the temperature decrease at the catalyst layer, advantageously promotes the aromatization reaction, and can improve the yield of the aromatic hydrocarbon. In addition, the partial pressure of hydrogen generated in the conversion reaction of the raw material can be reduced by recycling, the aromatization reaction can be promoted advantageously, and as a result, the yield of the aromatic hydrocarbon can be improved. Further, since the speed of gas in the reaction layer is increased (GHSV is increased), the contact time between the reaction substrate and the catalytic active site is shortened, and the excessive reaction that gives a coke-like substance can be suppressed.

As a result, the decrease in activity that occurs as the reaction time passes can be suppressed, and the yield of the aromatic hydrocarbon can be maintained at a high level. In commercial devices, the recycling gas ratio is determined from an economic point of view.

EXAMPLES

Hereinafter, the present invention will be more specifically described according to Examples, but the present invention is not limited to Examples below.

Synthesis Example (Production Example 1)

Using 5 g of ZSM-5 (an ammonium type, Si/Al=35 mol/mol), baking was performed at 500° C. for 5 hours under air flow to obtain ZSM-5 (a proton type). Subsequently, 0.37 g of gallium nitrate was dissolved in 70 ml of distilled water and suspended so that an aqueous solution of 3.0% by mass (a value in a case where the total mass of ZSM-5 was 100% by mass) of gallium was ion-exchanged (or impregnated and supported) and stiffed at 80° C. for 24 hours. Then, baking was performed at 500° C. for 3 hours under air flow, thereby obtaining a gallium-containing crystalline aluminosilicate. As a surface acidic point treatment, the gallium-containing crystalline aluminosilicate was stirred in tetramethoxysilane and hexane, refluxed for 1 hour, and then subjected to heating treatment at 600° C. Tableting molding was performed by applying a pressure of 39.2 MPa (400 kgf) and coarse pulverization was performed to make a granular material having a size of 20 to 28 meshes, thereby obtaining a crystalline aluminosilicate 1 (a catalyst composition 1) containing gallium. This crystalline aluminosilicate 1 was used as a catalyst composition for producing a monocyclic aromatic hydrocarbon having 6 to 8 carbon atoms in Example 1.

Production Example 2

A catalyst composition 2 was obtained in the same manner as in Production example 1 except that ZSM-5 having Si/Al=60 mol/mol was used.

Comparative Production Example

A comparative catalyst composition 1 was obtained in the same manner as in Production example 1 except that the surface acidic point treatment was not performed.

Comparative Production Example 2

A comparative catalyst composition 2 was obtained in the same manner as in Production example 2 except that the surface acidic point treatment was not performed.

<NH$_3$-TPD Measurement>

As a pretreatment, helium was made to flow to 30 mg of the sample at 30 mL/min, and the temperature was raised to 500° C. at a temperature raising rate of 10° C/min and held for 1 hour. After holding for 1 hour, the temperature was lowered to 100° C. under helium flow, and then ammonia (5% helium balance) was made to flow at 30 mL/min and held at 100° C. for 30 minutes. Next, helium was made to flow at 30 mL/min while being held at 100° C. to replace the inside of the system for 10 minutes, and then TPD measurement was performed while raising the temperature to 600° C. at a temperature raising rate of 10° C/min under a helium flow of 30 mL/min. The measurement results of the NH$_3$ acid quantity are shown in Table 1. It is noted that Al in the table was calculated from the atomic weight of each element assuming that the composition of ZSM-5 was $H^+n(H_2O)_{16}[Al_nSi_{96-n}O_{192}]$.

TABLE 1

| Catalyst composition | Comparative catalyst composition 1 | Catalyst composition 1 | Comparative catalyst composition 2 | Catalyst composition 2 |
|---|---|---|---|---|
| Si/Al | 35 | 35 | 60 | 60 |
| Acidic point treatment | No | Yes | No | Yes |
| Al | 0.42 mmol/g | 0.42 mmol/g | 0.25 mmol/g | 0.25 mmol/g |
| $NH_3$ acid quantity | 0.55 mmol/g | 0.44 mmol/g | 0.37 mmol/g | 0.30 mmol/g |
| $NH_3$ acid quantity/Al | 1.31 | 1.05 | 1.48 | 1.20 |

<BTX Yield (1)>

Examples 1 to 2 and Comparative Examples 1 and 2

Using a flow type reaction device having a reactor which was filled with 5 mL of the catalyst composition of each of Production Examples 1 and 2 and Comparative Production Examples 1 and 2, butene was brought into contact with the catalyst composition to be reacted under the conditions of a reaction temperature of 550° C. and a reaction pressure of 0.1 MPaG. At that time, nitrogen was introduced as a diluent so that the contact time between the raw material oil and the catalyst was 6.4 seconds.

The reaction was carried out under these conditions for 30 minutes to produce a monocyclic aromatic hydrocarbon having 6 to 8 carbon atoms, the composition of the product was analyzed by an FID gas chromatograph directly connected to the reaction device, and the yield of the monocyclic aromatic hydrocarbon having 6 to 8 carbon atoms was measured. The measurement results are shown in Table 2.

TABLE 2

| Catalyst composition | Comparative Example 1 Comparative catalyst composition 1 | Example 1 Catalyst composition 1 | Comparative Example 2 Comparative catalyst composition 2 | Example 2 Catalyst composition 2 |
|---|---|---|---|---|
| Si/Al | 35 | 35 | 60 | 60 |
| Acidic point treatment | No | Yes | No | Yes |
| BTX yield | 60 mass % | 64 mass % | 53 mass % | 65 mass % |

As shown in Table 2, in Example 1 to which the present invention was applied, the BTX yield was high as compared with that of Comparative Example 1 in which the comparative catalyst composition 1 which was not subjected to the acidic point surface treatment was used. In addition, in Example 2 to which the present invention was applied, the BTX yield was high as compared with that of Comparative Example 2 in which the comparative catalyst composition 2 which was not subjected to the acidic point surface treatment was used.

<BTX yield (2)>

Example 3 and Comparative Example 3

The yield of the monocyclic aromatic hydrocarbon having 6 to 8 carbon atoms was measured in the same manner as in the above-described "BTX yield (1)" except that butane was used instead of butene. The measurement results are shown in Table 3.

TABLE 3

| Catalyst composition | Comparative Example 3 Comparative catalyst composition 1 | Example 3 Catalyst composition 1 |
|---|---|---|
| Si/Al | 35 | 35 |
| Acidic point treatment | No | Yes |
| BTX yield | 50 mass % | 52 mass % |

As shown in Table 3, in Example 3 to which the present invention was applied, the BTX yield was high as compared with that of Comparative Example 3 in which the comparative catalyst composition 1 which was not subjected to the acidic point surface treatment was used.

<BTX yield (3)>

Example 4 and Comparative Example 4

The yield of the monocyclic aromatic hydrocarbon having 6 to 8 carbon atoms was measured in the same manner as in the above-described "BTX yield (1)" except that a raw material oil 1 having the properties described in Table 4 was used instead of butene. The measurement results are shown in Table 5.

TABLE 4

| Term | Light hydrocarbon | Analysis method |
|---|---|---|
| Density [g/cm³], 15° C. | 0.6522 g/cm³ | JIS K2249 |
| Distillation property ° C. | | |
| Distillation initial boiling point (IBP) | 34° C. | JIS K2254 |
| 10% by volume distilling temperature (T10) | 43° C. | |
| 90% by volume distilling temperature (T90) | 64° C. | |
| Distillation end point (EP) | 69° C. | |
| Composition vol % | | |
| Normal paraffin (C4 to C7) | 47.91 vol % | JIS K2536-2 Total composition analysis (gas chromatography) |
| Isoparaffin (C4 to C7) | 45.33 vol % | |
| Olefins | 0.01 vol % | |
| Naphthenes | 5.49 vol % | |
| Monocyclic aromatics | 1.27 vol % | |

TABLE 5

| Catalyst composition | Comparative Example 4 Comparative catalyst composition 1 | Example 4 Catalyst composition 1 |
|---|---|---|
| Si/Al | 35 | 35 |
| Acidic point treatment | No | Yes |
| BTX yield | 58 mass % | 61 mass % |

As shown in Table 5, in Example 4 to which the present invention was applied, the BTX yield was high as compared with that of Comparative Example 4 in which the comparative catalyst composition 1 which was not subjected to the acidic point surface treatment was used.

The preferred Examples of the present invention have been described above, but the present invention is not limited to these Examples. Additions, omissions, substitutions, and other modifications of the configuration can be made without departing from the gist of the present invention. The present invention is not limited by the description described above and is limited only by the scope of the attached Claims.

What is claimed is:

1. A method for producing a monocyclic aromatic hydrocarbon having 6 to 8 carbon atoms, the method comprising:
    heating and stirring a catalyst containing a crystalline aluminosilicate and a compound represented by General Formula (1) in a nitrogen atmosphere at 50° C. to 110° C., followed by heat treatment at 300° C. to 600° C. in the presence of oxygen, to obtain a catalyst composition coated with an amorphous silicon oxide compound, and
    bringing a raw material which contains a light hydrocarbon having 2 to 7 carbon atoms as a main component into contact with the catalyst composition to produce a monocyclic aromatic hydrocarbon having 6 to 8 carbon atoms;
wherein the compound represented by Formula (1) is:

$$X_n Si(OR)_{4-n} \qquad (1)$$

wherein X represents a hydrogen atom or an alkyl group, R represents an alkyl group, and n represents an integer of 0 to 4.

2. The method for producing a monocyclic aromatic hydrocarbon having 6 to 8 carbon atoms according to claim 1, wherein a molar ratio of an acid quantity of the catalyst composition to Al is 1.25 or less, the acid quantity being defined by an amount of ammonia desorbed in a temperature range of 200° C. to 500° C. in an $NH_3$-TPD method.

3. The method for producing a monocyclic aromatic hydrocarbon having 6 to 8 carbon atoms according to claim 1, wherein the crystalline aluminosilicate is a pentasil zeolite.

4. The method for producing a monocyclic aromatic hydrocarbon having 6 to 8 carbon atoms according to claim 3, wherein the crystalline aluminosilicate is an MFI zeolite.

5. The method for producing a monocyclic aromatic hydrocarbon having 6 to 8 carbon atoms according to claim 1, wherein a content of gallium with respect to 100 parts by mass of the catalyst composition for producing a monocyclic aromatic hydrocarbon is 0.1 parts by mass or more and 10.0 parts by mass or less.

6. The method for producing a monocyclic aromatic hydrocarbon having 6 to 8 carbon atoms according to claim 1, wherein the crystalline aluminosilicate contains gallium, and
    a molar ratio (Ga/Al) of gallium to aluminum is 0.1 or more and 10.0 or less.

* * * * *